United States Patent
Pamukcu et al.

(10) Patent No.: US 6,268,372 B1
(45) Date of Patent: Jul. 31, 2001

(54) METHOD FOR INHIBITING NEOPLASTIC CELLS AND RELATED CONDITIONS BY EXPOSURE TO 2,9-DISUBSTITUTED PURIN-6-ONES

(75) Inventors: Rifat Pamukcu, Spring House; Gary A. Piazza, Doylestown, both of PA (US)

(73) Assignee: Cell Pathways, Inc., Horsham, PA (US)

( * ) Notice: Subject to any disclaimer, the term of this patent is extended or adjusted under 35 U.S.C. 154(b) by 0 days.

(21) Appl. No.: 09/151,665

(22) Filed: Sep. 11, 1998

(51) Int. Cl.$^7$ .......................... A61K 31/52; A61K 31/655
(52) U.S. Cl. ............................................. 514/262; 514/150
(58) Field of Search ...................... 514/262, 150

(56) References Cited

U.S. PATENT DOCUMENTS

| | | |
|---|---|---|
| 3,031,450 | 4/1962 | Fischer et al. . |
| 3,161,654 | 12/1964 | Shen . |
| 3,322,755 | 5/1967 | Roch et al. . |
| 3,517,005 | 6/1970 | Cronin et al. . |
| 3,594,480 | 7/1971 | Cronin et al. . |
| 3,647,858 | 3/1972 | Hinkley et al. . |
| 3,654,349 | 4/1972 | Shen et al. . |

(List continued on next page.)

FOREIGN PATENT DOCUMENTS

| | | |
|---|---|---|
| 3038166 | 6/1981 | (DE) . |
| 0 347146 A2 | 12/1989 | (EP) . |
| 274218 | 12/1989 | (DE) . |
| 0 349239 A2 | 1/1990 | (EP) . |
| 0 351058 | 1/1990 | (EP) . |
| 0 352960 A2 | 1/1990 | (EP) . |
| 0 395328 A2 | 10/1990 | (EP) . |
| 0 428268 A2 | 5/1991 | (EP) . |
| 0 463756 A1 | 1/1992 | (EP) . |
| 0 485157 A2 | 5/1992 | (EP) . |
| 0 485158 A2 | 5/1992 | (EP) . |
| 0 485171 A2 | 5/1992 | (EP) . |
| 0 485172 A2 | 5/1992 | (EP) . |
| 0 485173 A2 | 5/1992 | (EP) . |
| 0 508586 A1 | 10/1992 | (EP) . |
| 0 526004 A1 | 2/1993 | (EP) . |
| 0 607439 A1 | 7/1994 | (EP) . |
| 0 722 943 A1 | 1/1996 | (EP) . |
| 0 722 944 A1 | 1/1996 | (EP) . |
| 807826 | 1/1959 | (GB) . |
| 2063249 | 6/1981 | (GB) . |
| 56-53659 | 5/1981 | (JP) . |
| 57-167974 | 10/1982 | (JP) . |
| WO 92/03419 | 3/1992 | (WO) . |
| WO 93/07149 | 4/1993 | (WO) . |
| WO 93/12095 | 6/1993 | (WO) . |
| WO 94/05661 | 3/1994 | (WO) . |
| WO 95/19978 | 7/1995 | (WO) . |
| WO 97/03985 | 2/1997 | (WO) . |

OTHER PUBLICATIONS

Blaya, C. et al., Effect of the Protein kinase inhibitors, 1–(5–isoquinolinylsulfonyl)–2–methylpiperazine H–7 and N–(2–[methylamino]ethyl)–5–isoquinoline–sulfonamide H–8 on Lewis lung carcinoma tumor progression, European Journal of Pharmacology, 354, pp. 99–104 (1998).

Chang, W. et al., Sulindac Sulfone Modulates the Expression and Cellular Localization of b–Catenin in Human Colon Carcinoma Cells, Digestive Disease Week, Apr. 1, 1999.

Earnest, D. et al., Piroxicam and Other Cyclooxygenase Inhibitors: Potential for Cancer Chemoprevention, Journal of Cellular Biochemistry, Supplement 161:156–166 (1992).

Easwaran, V. et al., The Ubiquitin–Proteasome Pathway and Serine Kinase Activity Modulate Adenomatous Polyposis Coli Protein–mediated Regulation of β–Catenin–Lymphocyte Enhancer–binding Factor Signaling, The Journal of Biological Chemistry, vol. 274, No. 23, pp. 16641–16645, Jun. 4, 1999.

Jiang, X. et al., Inhibition of calmodulin–dependent phosphodiesterase induces apoptosis in human leukemic cells, Proc. Natl. Acad. Sci. USA, vol. 83, pp. 11236–11241, Oct. 1996.

Korinek, V. et al., Constitutive Transcriptional Activation by a β–Catenin–Tcf Complex in APC$^{-/-}$Colon Carcinoma, Science, vol. 275, pp. 1784–1786, Mar. 21, 1997.

Mahmoud, N. et al., Apc Gene Mutation is Associated with a Dominant–Negative Effect upon Intestinal Cell Migration, Cancer Research 57, pp. 5045–5050, Nov. 15, 1997.

Mahmoud, N. et al., Genotype–Phenotype Correlation in Murine Apc Mutation: Differences in Enterocyte Migration and Response to Sulindac, Cancer Research 59, pp. 353–359, Jan. 15, 1999.

Morin, P. et al., Activation of β–Catenin–Tcf Signaling in Colon Cancer by Mutations in β–Catenin or APC, Science, vol. 275, pp. 1787–1789, Mar. 21, 1997.

Peifer, M., β–Catenin as Oncogene: The Smoking Gun, Science, vol. 275, pp. 1752–1753, Mar. 21, 1997.

Rubinfeld, B. et al., Stabilization of βCatenin by Genetic Defects in Melanoma Cell Lines, Science, vol. 275, pp. 1790–1792, Mar. 21, 1997.

Waddell, W.R. et al., Am. J. Surgery, vol. 157, pp. 175–179 (1989).

Gonzaga, R.A.F. et al., The Lancet, Mar. 30, 1985, p. 751.

Waddell, W.R. et al., J. Surg. Oncology, vol. 24, pp. 83–87 (1983).

Federation Proceedings (1972) of the Federation of American Societies for Experimental Biology abstract Nos. 2044 and 2045.

(List continued on next page.)

Primary Examiner—Jerome D. Goldberg
(74) Attorney, Agent, or Firm—Robert W. Stevenson

(57) ABSTRACT

A method for inhibiting the growth of neoplastic cells by exposure to 2,9-disubstituted purin-6-ones.

6 Claims, No Drawings

U.S. PATENT DOCUMENTS

| | | |
|---|---|---|
| 3,780,040 | 12/1973 | Schnettler et al. . |
| 3,812,127 | 5/1974 | Cronin et al. . |
| 3,819,631 | 6/1974 | Broughton et al. . |
| 3,920,636 | 11/1975 | Takahasi et al. . |
| 4,001,237 | 1/1977 | Partyka et al. . |
| 4,001,238 | 1/1977 | Partyka et al. . |
| 4,039,544 | 8/1977 | Broughton et al. . |
| 4,060,615 | 11/1977 | Matier et al. . |
| 4,079,057 | 3/1978 | Juby et al. . |
| 4,098,788 | 7/1978 | Crenshaw et al. . |
| 4,101,548 | 7/1978 | Crenshaw et al. . |
| 4,102,885 | 7/1978 | Crenshaw et al. . |
| 4,138,561 | 2/1979 | Crenshaw et al. . |
| 4,146,718 | 3/1979 | Jenks et al. . |
| 4,161,595 | 7/1979 | Kaplan et al. . |
| 4,171,363 | 10/1979 | Crenshaw et al. . |
| 4,208,521 | 6/1980 | Crenshaw et al. . |
| 4,209,623 | 6/1980 | Juby . |
| 4,423,075 | 12/1983 | Dvornik et al. . |
| 4,460,590 | 7/1984 | Möller . |
| 4,460,591 | 7/1984 | DeGraw et al. . |
| 4,880,810 | 11/1989 | Lowe, III et al. . |
| 4,885,301 | 12/1989 | Coates . |
| 4,923,874 | 5/1990 | McMahon et al. . |
| 4,950,680 | 8/1990 | Taylor et al. . |
| 5,073,559 | 12/1991 | Coates . |
| 5,147,875 | 9/1992 | Coates et al. . |
| 5,223,501 | 6/1993 | Chakravarty et al. . |
| 5,250,535 | 10/1993 | Verheyden et al. . |
| 5,254,571 | 10/1993 | Coates et al. . |
| 5,358,952 | 10/1994 | Moschel et al. . |
| 5,401,774 | 3/1995 | Pamukcu et al. . |
| 5,439,895 | 8/1995 | Lee et al. . |
| 5,488,055 | 1/1996 | Kumar et al. . |
| 5,614,530 | 3/1997 | Kumar et al. . |
| 5,614,627 | 3/1997 | Takase et al. . |
| 5,696,159 | 12/1997 | Gross et al. . |

OTHER PUBLICATIONS

Gilman, S.C. et al., Nonsteroidal Anti–inflammatory Drugs in Cancer Therapy, (circa 1985).

Brogden, R.N. et al., Drugs, vol. 16, pp. 97–114 (1978).

Hucker, H.B. et al., Drug Metabolism & Disposition, vol. 1, No. 6, pp. 721–736 (1973).

Shen, T.Y. et al., Chemical and Biological Studies on Indomethacin, Sulindac and Their Analogs, pp. 107–178 (circa 1975).

Duggan, D.E. et al., Clin. Pharm. & Therapeutics, vol. 21, No. 3, pp. 326–335 (1976).

Duggan, D.E. et al., J. Pharm. & Exper. Therap., vol. 201, No. 1, pp. 8–13 (1977).

Glavin, G.B. et al., Toxicology and Applied Pharmacology, vol. 83, pp. 386–389 (1986).

Moorghen, M. et al., Journal of Pathology, vol. 156, pp. 341–347 (1988).

Moorghen, M. et al., Acta Histochemica, Suppl.–Band XXIX, S. 195–199 (1990).

Bjarnason et al., Gastroenterology, vol. 94, No. 4, pp. 1070–1074 (1988).

Badrieh, Y., et al., Chem. Ber., vol. 125, pp. 667–674 (1992).

Silvola, J. et al., Effects ofnonsteroidal anti–inflammatory drugs on rat gastric mucosal phosphodiesterase activity, Agents and Actions, vol. 12.4, pp. 516–520 (1982).

Curtis–Prior, P.B. et al., Cyclic Nucleotide Phosphodiesterase Activity of Human Normal and Carcinomatous Lung Tiussue, The Lancet, pp. 1225–1225 Dec. 4, 1976.

Pepin, P. et al., Effects of Sulindac and Oltipraz on the tumorigenicity of 4–(methylnitrosamino)1–(3–pyridyl)–1–Butanone in A/J mouse lung, Carcinogenesis, vol. 13, No. 3, pp. 341–348 (1992).

Nicholson, C.D. et al. Differential modulation of tissue function and therapeutic potential of selective inhibitors of cyclic nucleotide phosphodiesterase isoenzymes, Trends Pharmacol. Sci. (TiPS), vol. 12, pp. 19–27 (1991).

Ahn, H.S. et al., Effects of Selective Inhibitors on Cyclic Nucleotide Phosphodiesterases of Rabbit Aorta, Biochemical Pharmacology, vol. 38, No. 19, pp. 3331–3339 (1989).

Luginer, C. et al., Selective Inhibition of Cyclic Nucleotide Phosphodiesterases of Human, Bovine and Rat Aorta, Biochem. Pharmacology, vol. 35, No. 10, pp. 1743–1751 (1986).

Turner, N.C. et al., Relaxation of guinea–pig trachea by cyclic AMP phosphodiesterase inhibitors and their enhancement by sodium mitroprusside, Br. J. Pharmacol. Vol. III, pp. 1047–1052 (1994).

Weishaar, R.E. et al., Multiple Molecular Forms of Cyclic Nucleotide Phosphodiesterase in Cardiac and Smooth Muscle and In Platelets, Biochem. Pharmacology, vol. 35, No. 5, pp. 787–800 (1986).

Murray, K.J. et al., Potential Use of Selective Phosphodiesterase Inhibitors in the Treatment of Asthma, New Drugs for Asthma Therapy, Birkhauser Verlag Basel, pp. 27–46 (1991).

Saeki, T. et al., Isolation of Cyclic Nucleotide Phosphodiesterase Isozymes From Pig Aorta, Biochem. Pharmacology, vol. 46, No. 5, pp. 833–839 (1993).

Turner, N.C. et al., Pulmonary effects of type V cyclic GMP specific phosphodiesterase inhibition in anaesthetized guine-a–pig, Br. J. Pharmacol., vol. 111, 1198–1204 (1994).

Ferreira, S.H. et al., The molecular mechanism of action of peripheral morphone analgesia: stimulation of the cGMP system via nitric oxide release, European Journal of Pharmacology, 201 pp. 121–122 (1991).

Hidaka, H. et al., Selective Inhibitors of Three Forms of Cyclic Nucleotide Phosphodiesterase—Basic and Potential Clinical Applications, vol. 16, Advances in Cyclic Nucleotide and Protein Phosphorylation Research, pp. 245–259 (1984).

Tulshian, D. et al., Synthesis and Phosphodiesterase Activity of Carboxylic Acid Mimetics of Cyclic Guanosine 3", 5"–Monophosphate, J. Med. Chem, vol. 36, 1210–1220 (1993).

Yasumoto, T. et al., Properties of Base–Substituted and Carboxyl–Esterified Analogues of Griseolic Acid, a Potent cAMP Phosphodiesterase Inhibitor, Biochemical Pharmacology, vol. 43, No. 10, pp. 2073,2081 (1992).

Broughton, B.J. et al., Antiallergic Activity of 2–Phenyl–8–azapruin–6–ones, Journal of Medicinal Chemistry, vol. 18, No. 11, pp. 1117–1118 (1975).

Kodoma, K. et al., Effects of a novel, selective and potent phosphodiesterase type V inhibitor, E4021, on myocardial ischemia in guinea pigs, Euro. J. of Pharma. 263, pp. 93–99 (1994).

Zacharski, L. R. et al., Effect of Mopidamol on Survival in Carcinoma of the Lung and Colon: Final Report of Veterans Administration Cooperative Study No. 188, J. of the Nat'l. Cancer Inst., vol. 80, No. 2, pp. 90–96 (1988).

Lichtner, R. B. et al., The Pyrimido–pyrimidine Derivatives RA 233 adn RX–RA 85 affect Growth and Cytoskeletal Organization of Rat Mammary Adenocarcinoma Cells, Eur. J. Cancer Clin. Oncol., vol. 23, No. 9, pp. 1269–1275 (1987).

Janik, P. et al., Inhibition of Growth of Primary and Metastatic Lewis Lung Carcinoma Cells by the Phosphodiesterase Inhibitor Isobutylmethylxanthine, Cancer Res. vol. 40, pp. 1950–1954, (Jun., 1980).

Bergstrand, Hakan et al., Effects of Antiallergic Agents, Compound 48/80, and Some Reference Inhibitors on the Activity of Partially Purified Human Lung Tissue Adenosine Cyclic 3',5'–Monophosphage and Guanosine Cyclic 3'–5'–Monophosphate Phosphodiesterases, Molecular Pharmacology, 13, pp. 38–43 (1976).

Drees, Markus et al., 3',5'–Cyclic Nucleotide Phosphodiesterase in Tumor Cells as Potential Target for Tumor Growth Inhibition, Cancer Research 53, pp. 3058–3061 (1993).

Semmler, J. et al., Xanthine derivatives: comparison between suppression of tumor necrosis factor–x production and inhibition of cAMP phosphodiesterase activity, Immunology 78, pp. 520–525 (1993).

Mehta, Rajendra et al., Structure–Activity Relationships of Brassinin in Preventing the Development of Carcinogen–Induced Mammary Lesions in Organ Culture, Anticancer Research 14: 1209–1214 (1994).

Makaryan, A.P. et al., Cyclic Nucleotides in Patients with Malignant Neoplasms of the Colon, Laboratornoe Delo, vol. 8, pp. 31–33 (1991).

Carter et al., Chemotherapy of Cancer, $2^{nd}$ Ed., John Wiley & Sons, NY, NY, 1981, pp. 362–365.

Biddle, William et al., Antineoplastic Effect of the Pyrimido–Pyrimidine Derivative: RA 233, Pathologie Biologie, Jan., 1984, pp. 9–13.

Clarke, W.R. et al., The type III phosphodiesterase inhibitor milrinone and type V PDE inhibitor dipyridamole individually and synergistically reduce elevated pulmonary vascular resistance (Abstract Only), Pulm. Pharmacol., 7(2), pp. 81–9, (1994).

Raeburn, David et al., Effects of isoenzyme–selective inhibitors of cyclic nucleotide phosphodiesterase on microvascular leak in guinea pig airways in vivo (Abstract Only), J. Pharmacol. Exp. Ther., 267(3), pp. 1147–1151 (1993).

Marcoz, P. et al., Modulation of rat thymocyte proliferative response through the inhibition of different cyclic nucleotide phosphodiesterase isoforms by means of selective inhibitors and cGMP–elevating agents (Abstract Only), Mol. Pharmacol. 44(5) pp. 1027–1035 (1993).

Barnett, Mary S. et al., Initial biochemical and functional characterization of cyclic nucleotide phosphodiesterase isozymes in canine colonic smooth muscle (Abstract Only), J. Pharmacol. Exp. Ther., 264(2) pp. 801–812 (1993).

Molnar–Kimber, K. et al., Modulation of TNFa and IL–1B from indotoxin–stimulated monocytes by selective PDE isozyme inhibitors (Abstract Only), Agents Actions 39(Spec. Conf. Issue), C77–C79 (1993).

Giorgi, Mauro et al., Characterization of 3':5' cyclic nucleotide phosphodiesterase activities of mouse neuroblastoma N18TG2 cells (Abstract Only), FEBS Lett. 324(1) pp. 76–80 (1993).

Porter, Roderick et al., Preparation of 6–phenyl–3–(5–tetrazoly)pyridin–2(H)–one derivatives as cyclic AMP–dependent protein kinase agonists (Abstract Only), PCT Int. Appl. WO9206085 A1, (Sep. 26, 1991).

Molnar–Kimber, K. L. et al., Differential regulation of TNF–a and IL–1B production from endotoxin stimulated human monocytes by phosphodiesterase inhibitors (Abstract Only), Mediators Inflammation 1(6) pp. 411–417 (1992).

Radomski, Marek W. et al., Human Colorectal adenocarcinoma cells: differential nitric oxide synthesis determines their ability of aggregate platelets (Abstract Only), Cancer Res. 51(22) pp. 6073–6078 (1991).

Anderson, Thomas L. G. et al., Interactions between isoprenaline, sodium nitroprusside, and isozyme–selective phosphodiesterase inhibitors on ADP–induced aggregation and cyclic Nucleotide levels in human platelets (Abstract Only), J. Cardiovasc, Pharmacol. 18(2) pp. 237–242 (1991).

Souness, John E. et al., Role of Selective cyclic GMP phosphodiesterase inhibition in the myorelaxant actions of M&B 22,943, MY–5445, vinpocetine and 1–methyl–3–isobutyl–8–(methylamino)xanthine (Abstract Only), Br. J. Pharmacol. 98(3) pp. 725–735 (1989).

Lichtner, Rosemarie B., The pyrimidopyrimidine derivatives RA233 and RX–RA85 affect cell cycle distribution of two murine tumor cell lines (Abstract Only), Eur. J. Cancer Clin. Oncol. 25(6), pp. 945–951 (1989).

Mamytbekova, A., et al., Antimetastatic effect of flurbiprofen and other platelet aggregation inhibitors (Abstract Only), Neoplasma 33(4), pp. 417–421 (1986).

Hagiwara, Masatoshi et al., Effect of 1–(3–chloroanilino)–4–phenylpthalazine (MY–5445), a specific inhibitor of cyclic CMP phosphodiesterase, on human platelet aggregation (Abstract Only), J. Pharmacol. Exp. Ther. 229(2) pp. 467–471 (1984).

METHOD FOR INHIBITING NEOPLASTIC CELLS AND RELATED CONDITIONS BY EXPOSURE TO 2,9-DISUBSTITUTED PURIN-6-ONES

This invention relates to a method for the selective inhibition of neoplastic cells, for example, for the treatment or prevention of precancerous lesions or other neoplasias in mammals, in particular by using 2,9-disubstituted purin-6-ones as therapeutic agents.

BACKGROUND OF THE INVENTION

Each year in the United States alone, untold numbers of people develop precancerous lesions, which is a form of neoplasia, as discussed below. Such lesions exhibit a strong tendency to develop into malignant tumors, or cancer. Such lesions include lesions of the breast (that can develop into breast cancer), lesions of the skin (that can develop into malignant melanoma or basal cell carcinoma), colonic adenomatous polyps (that can develop into colon cancer), and other such neoplasms. Compounds that prevent or induce the remission of existing precancerous or cancerous lesions or carcinomas would greatly reduce illness and death from cancer.

For example, approximately 60,000 people die from colon cancer, and over 150,000 new cases of colon cancer are diagnosed each year. For the American population as a whole, individuals have a six percent lifetime risk of developing colon cancer, making it the second most prevalent form of cancer in the country. Colon cancer is also prevalent in Western Europe. It is believed that increased dietary fat consumption is increasing the risk of colon cancer in Japan.

In addition, the incidence of colon cancer reportedly increases with age, particularly after the age of 40. Since the mean ages of populations in America and Western Europe are increasing, the prevalence of colorectal cancer should increase in the future.

To date, little progress has been made in the prevention and treatment of colorectal cancer, as reflected by the lack of change in the five-year survival rate over the last few decades. The only cure for this cancer is surgery at an extremely early stage. Unfortunately, most of these cancers are discovered too late for surgical cure. In many cases, the patient does not experience symptoms until the cancer has progressed to a malignant stage.

In view of these grim statistics, efforts in recent years have concentrated on colon cancer prevention. Colon cancer usually arises from pre-existing benign neoplastic growths known as polyps. Prevention efforts have emphasized the identification and removal of colonic polyps. Polyps are identified by x-ray and/or colonoscopy, and usually removed by devices associated with the colonoscope. The increased use of colon x-rays and colonoscopies in recent years has detected clinically significant precancerous polyps in four to six times the number of individuals per year that acquire colon cancer. During the past five years alone, an estimated 3.5 to 5.5 million people in the United States have been diagnosed with adenomatous colonic polyps, and it is estimated that many more people have or are susceptible to developing this condition, but are as yet undiagnosed. In fact, there are estimates that 10–12 percent of people over the age of 40 will form clinically significant adenomatous polyps.

Removal of polyps has been accomplished either with surgery or fiber-optic endoscopic polypectomy—procedures that are uncomfortable, costly (the cost of a single polypectomy ranges between $1,000 and $1,500 for endoscopic treatment and more for surgery), and involve a small but significant risk of colon perforation which can be fatal. Overall, about $2.5 billion is spent annually in the United States in colon cancer treatment and prevention.

In the breast, breast cancer is often treated surgically, often by radical mastectomy with its painful and emotional aftermath. Such surgery is costly, too.

As indicated above, each lesion carries with it a chance that it will develop into a cancer. The likelihood of cancer is diminished if a precancerous lesion is removed. However, many of these patients demonstrate a propensity for developing additional lesions in the future. They must, therefore, be monitored periodically for the rest of their lives for reoccurrence.

In most cases (i.e. the cases of sporadic lesion formation, e.g. so-called common sporadic polyps), lesion removal will be effective to reduce the risk of cancer. In a small percentage of cases (i.e. cases where numerous lesions form, e.g. the so-called polyposis syndromes), removal of all or part of the effected area (e.g. the colon) is indicated. For example, the difference between common sporadic polyps and polyposis syndromes is dramatic. Common sporadic polyp cases are characterized by relatively few polyps that can usually be removed leaving the colon intact. By contrast, polyposis syndrome cases can be characterized by many (e.g. hundreds or more) of polyps—literally covering the colon in some cases—making safe removal of the polyps impossible short of surgical removal of the colon.

Because each lesion carries with it a palpable risk of cancerous development, patients who form many lesions (e.g. polyposis syndrome patients) invariably develop cancer if left untreated. Surgical removal of the colon is the conventional treatment in polyposis patients. Many polyposis patients have undergone a severe change in lifestyle as a result of the disfiguring surgery. Patients have strict dietary restrictions, and many must wear ostomy appliances to collect their intestinal wastes.

The search for drugs useful for treating and preventing cancer is intensive. Indeed, much of the focus of cancer research today is on the prevention of cancer because chemotherapy for cancer itself is often not effective and has severe side effects. Cancer chemoprevention is important for recovered cancer patients who retain a risk of cancer reoccurrence. Also, cancer prevention is important for people who have not yet had cancer, but have hereditary factors that place them at risk of developing cancer. With the development of new genetic screening technologies, it is easier to identify those patients with high-risk genetic factors, such as the potential for polyposis syndrome, who would greatly benefit from chemopreventative drugs. Therefore, finding such anti-cancer drugs that can be used for prolonged preventive use is of vital interest.

Known chemopreventative and chemotherapeutic drugs are believed to kill cancer cells by inducing apoptosis, or as sometimes referred to as "programmed cell death." Apoptosis naturally occurs in virtually all tissues of the body, and especially in self-renewing tissues such as bone marrow, gut, liver and skin. Apoptosis plays a critical role in tissue homeostasis, that is, it ensures that the number of new cells produced are correspondingly offset by an equal number of cells that die. For example, the cells in the intestinal lining divide so rapidly that the body must eliminate cells after only three days in order to prevent the overgrowth of the intestinal lining.

Recently, scientists have realized that abnormalities of apoptosis can lead to the formation of precancerous lesions and carcinomas. Also, recent research indicates that defects in apoptosis play a major role in other diseases in addition to cancer. Consequently, compounds that modulate apoptosis could be used to prevent or control cancer, as well as used in the treatment of other diseases.

Unfortunately, even though known chemotherapeutic drugs may exhibit such desirable apoptosis effects, most chemotherapeutic drugs have serious side effects that prohibit their long-term use, or use in otherwise healthy individuals with precancerous lesions. These side effects, which are a result of nonspecific cytotoxicity of the drugs, include hair loss, weight loss, vomiting, immune suppression and other toxicities. For this reason, there is a need to identify new drug candidates for therapy of patients with precancerous lesions that do not have such serious side effects in humans.

In recent years, several nonsteroidal anti-inflammatory drugs ("NSAIDs"), originally developed to treat arthritis, have shown effectiveness in inhibiting and eliminating colonic polyps. Polyps virtually disappear when the patients take such drugs, particularly when the NSAID sulindac is administered. However, the prophylactic use of currently available NSAIDs, even in polyposis syndrome patients, is marked by severe side reactions that include gastrointestinal irritations and ulcerations. Once NSAID treatment is terminated due to such complications, the polyps return, particularly in polyposis syndrome patients.

Sulindac has been particularly well received among the NSAIDs for the polyp treatment. Sulindac is a sulfoxide compound that itself is believed to be inactive as an antiarthritic agent. The sulfoxide is reportedly converted by liver enzymes to the corresponding sulfide, which is acknowledged to be the active moiety as a prostaglandin synthesis inhibitor. The sulfide, however, is associated with the side effects of conventional NSAIDs. The sulfoxide is also known to be metabolized to sulfone compound that has been found to be inactive as an inhibitor of prostaglandin synthesis but active as an inhibitor of precancerous lesions.

SUMMARY OF THE INVENTION

This invention includes a method of inhibiting neoplastic cells by exposing those cells to a pharmacologically effective amount of those compounds described below. Such compounds are effective in modulating apoptosis and eliminating and inhibiting the growth of neoplasias such as precancerous lesions.

The compounds that are useful in the methods of this invention include those of Formula I below.

DETAILED DESCRIPTION OF THE INVENTION

The present invention is a method of treating a patient with neoplastic lesions by administering to a patient a pharmacologically effective amount of a pharmaceutical composition that includes a 2,9-disubstituted purin-6-one of Formula I:

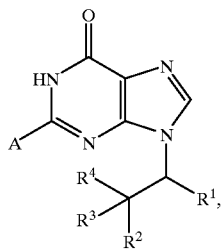

(I)

wherein $R_1$ is selected from the group consisting of straight-chain or branched alkyl with 2 to 10 carbon atoms, which is optionally substituted by phenyl, which in turn may be substituted by halogen, nitro, cyano, or by straight-chain or branched alkyl with up to 6 carbon atoms;

$R_2$ is selected from the group consisting of hydrogen, hydroxy, azido, or a straight-chain or branched alkyl with up to 6 carbon atoms, or a group with the formula —O—SO$_2$R$_5$;

$R_5$ is selected from the group consisting of a straight-chain or branched alkyl with up to 4 carbon atoms or phenyl;

$R_3$ is selected from the group consisting of hydrogen or $R_2$ and $R_3$ together form a group of the formula =O;

$R_4$ is selected from the group consisting of hydrogen or a straight-chain or branched alkyl with up to 4 carbon atoms; and A is selected from the group consisting of a moiety of the formula:

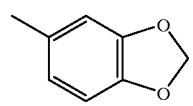

or a straight-chain or branched alkyl with up to 20 carbon atoms, or a cycloalkyl with 3 to 7 carbon atoms, phenyl wherein said moiety, alkyl, cycloalkyl or phenyl groups are optionally substituted with one or two groups independently selected from the group consisting of halogen, carboxyl, trifluoromethyl, nitro, cyano, or straight-chain or branched alkyl, alkoxycarbonyl, or alkoxy, each with up to 5 carbon atoms, which in turn may be substituted by phenyl, said ring structures optionally substituted by phenyl, which in turn may be substituted by straight-chain or branched alkoxy with up to 5 carbon atoms; and their tautomers and salts.

Physiologically acceptable salts are preferred in the practice of the invention. Physiologically acceptable salts can be salts of the compounds pursuant to the invention with inorganic or organic acids. Preferred salts are those with inorganic acids, for example hydrochloric acid, hydrobromic acid, phosphoric acid, or sulfuric acid, or salts with organic carboxylic acids or sulfonic acids, for example acetic acid, maleic acid, fumaric acid, malic acid, citric acid, tartaric acid, lactic acid, benzoic acid, or methanesulfonic acid, ethanesulfonic acid, benzenesulfonic acid, toluenesulfonic acid, or naphthalenedisulfonic acid.

The compounds of Formula (I) can occur in various stereochemical forms, which have the nature either of image and mirror image (enantiomers) or which are not mirror images of one another (diastereoisomers). The invention involves the use of both the antipodes and the racemic forms, and mixtures of diastereoisomers. The racemic forms can be separated, as can the diastereoisomers, into their stereoisomerically pure components, by known methods.

Preferred compounds of Formula (1) are those in which $R_1$ is selected from the group consisting of straight-chain or branched alkyl with 2 to 8 carbon atoms, which is optionally substituted by phenyl, which in turn may be substituted by fluorine; chlorine, bromine, nitro, cyano, or by straight-chain or branched alkyl with up to 4 carbon atoms, $R_2$ is selected from the group consisting of hydrogen, hydroxy, azido, or for straight-chain or branched alkyl with up to 4 carbon atoms, or a group with the formula —O—$SO_2R_5$;

$R_5$ is selected from the group consisting of straight-chain or branched alkyl with up to 3 carbon atoms, or phenyl;

$R_3$ is selected from the group consisting of hydrogen, or $R_2$ and $R_3$ jointly form the group of the formula =O;

$R_4$ is selected from the group consisting of hydrogen or for straight-chain or branched alkyl with up to 3 carbon atoms; and A is selected from the group consisting of a group with the formula

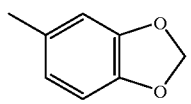

or straight-chain or branched alkyl with up to 19 carbon atoms, or for cyclopropyl, cyclopentyl, cyclohexyl, cycloheptyl, or for phenyl, which optionally are substituted up to twice with the same or different substituents consisting of fluorine, chlorine, bromine, carboxyl, nitro, hydroxy, or by straight-chain or branched alkyl, alkoxycarbonyl, or alkoxy, each with up to 4 carbon atoms, which in turn may be substituted by phenyl, and/or the rings are optionally substituted by phenyl, which in turn may be substituted by straight-chain or branched alkoxy with up to 4 carbon atoms and their tautomers and salts.

Especially preferred are compounds of Formula I in which $R_1$ is selected from the group consisting of straight-chain or branched alkyl with 2 to 7 carbon atoms, which is optionally substituted by phenyl, which in turn may be substituted by fluorine, chlorine, bromine, nitro, cyano, or by straight-chain or branched alkyl with up to 3 carbon atoms;

$R_2$ is selected from the group consisting of hydrogen, hydroxy, azido, or for straight-chain or branched alkyl with up to 3 carbon atoms, or for a group with the formula —O—$SO_2R_5$;

$R_5$ is selected from the group consisting of straight-chain or branched alkyl with up to 3 carbon atoms or phenyl, $R_3$ is selected from the group consisting of hydrogen or $R_2$ and $R_3$ jointly form the group of the formula =O, $R_4$ is selected from the group consisting of hydrogen or a straight-chain or branched alkyl with up to 3 carbon atoms; and A is selected from the group consisting of a group of the formula

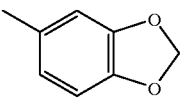

or for straight-chain or branched alkyl with up to 18 carbon atoms, or cyclopropyl, cyclopentyl, cyclohexyl, cycloheptyl, or for phenyl, which optionally are substituted up to twice with the same or different substituents consisting of fluorine, chlorine, bromine, carboxyl, nitro, hydroxy, or by straight-chain or branched alkyl, alkoxycarbonyl, or alkoxy, each with up to 3 carbon atoms, which in turn may be substituted by phenyl, and/or the rings are optionally substituted by phenyl, which in turn may be substituted by straight-chain or branched alkoxy with up to 3 carbon atoms and their tautomers and salts.

The present invention is also a method of treating individuals with neoplastic lesions by administering a pharmacologically effective amount of an enterically coated pharmaceutical composition that includes compounds of this invention.

Also, the present invention is a method of inhibiting the growth of neoplastic cells by exposing the cells to an effective amount of compounds of Formula I, wherein $R_1$ etc. are defined as above.

In still another form, the invention is a method of inducing apoptosis in human cells by exposing those cells to an effective amount of compounds of Formula I, wherein $R_1$ etc. are defined as above where such cells are sensitive to these compounds.

Additionally, in yet another form, the invention is a method of treating a patient having a disease which would benefit from regulation of apoptosis by treating the patient with an effective amount of compounds of Formula I, wherein $R_1$ etc. are defined as above. The regulation of apoptosis is believed to play an important role in diseases associated with abnormalities of cellular growth patterns such as benign prostatic hyperplasia, neurodegenerative diseases such as Parkinson's disease, autoimmune diseases including multiple sclerosis and rheumatoid arthritis, infectious diseases such as AIDS, and other diseases, as well.

As used herein, the term "precancerous lesion" includes syndromes represented by abnormal neoplastic, including dysplastic, changes of tissue. Examples include dysplasic growths in colonic, breast, bladder or lung tissues, or conditions such as dysplastic nevus syndrome, a precursor to malignant melanoma of the skin. Examples also include, in addition to dysplastic nevus syndromes, polyposis syndromes, colonic polyps, precancerous lesions of the cervix (i.e., cervical dysplasia), esophagus, prostatic dysplasia, bronchial dysplasia, breast, bladder and/or skin and related conditions (e.g., actinic keratosis), whether the lesions are clinically identifiable or not.

As used herein, the term "carcinomas" refers to lesions that are cancerous. Examples include malignant melanomas, breast cancer, prostate cancer and colon cancer.

As used herein, the term "neoplasm" refers to both precancerous and cancerous lesions and hyperplasia.

Compounds useful in the practice of this invention may be formulated into pharmaceutical compositions together with pharmaceutically acceptable carriers for oral administration in solid or liquid form, or for rectal or topical administration, although carriers for oral and parenteral administration are most preferred.

Pharmaceutically acceptable carriers for oral administration include capsules, tablets, pills, powders, troches and granules. In such solid dosage forms, the carrier can comprise at least one inert diluent such as sucrose, lactose or starch. Such carriers can also comprise, as is normal practice, additional substances other than diluents, e.g., lubricating agents such as magnesium stearate. In the case of capsules, tablets, troches and pills, the carriers may also comprise buffering agents. Carriers such as tablets, pills and granules can be prepared with enteric coatings on the surfaces of the tablets, pills or granules. Alternatively, the enterically coated compound can be pressed into a tablet, pill, or granule, and the tablet, pill or granules for administration to the patient. Preferred enteric coatings include those that dissolve or disintegrate at colonic pH such as shellac or Eudraget S.

Pharmaceutically acceptable carriers include liquid dosage forms for oral administration, e.g., pharmaceutically acceptable emulsions, solutions, suspensions, syrups and elixirs containing inert diluents commonly used in the art, such as water. Besides such inert diluents, compositions can also include adjuvants such as wetting agents, emulsifying and suspending agents, and sweetening, flavoring and perfuming agents.

Pharmaceutically acceptable carriers for topical administration include DMSO, alcohol or propylene glycol and the like that can be employed with patches or other liquid-retaining material to hold the medicament in place on the skin so that the medicament will not dry out.

Pharmaceutically acceptable carriers for rectal administration are preferably suppositories that may contain, in addition to the compounds of this invention excipients such as cocoa butter or a suppository wax, or gel.

When the present invention is used as a medicine for such diseases, it is administered by oral, intravenous or parenteral administration. The dose thereof varies depending upon the extent of symptom; the age, sex, weight and drug sensitivity of a patient; the method, timing and interval of administration; the type of pharmaceutical preparation; the type of a medicine to be administered together therewith; the type of an active ingredient and so forth.

With intravenous administration, it is recommended to administer amounts of about 0.01 to 10 mg/kg of body weight, preferably about 0.1 to 10 mg/kg. Nevertheless, it may be necessary to deviate from the amounts mentioned, specifically depending on the body weight or the method of administration, on individual behavior toward the medication, on the type of formulation, and the time or intervals at which administration occurs. Thus, in some cases, it may be sufficient to get by with less than the aforementioned minimum amounts, while in other cases the mentioned upper limits have to be exceeded. It may be advisable when administering larger amounts to divide them into several individual doses throughout the day.

A method for preparing the compounds of Formula I involves reacting compounds of Formula II

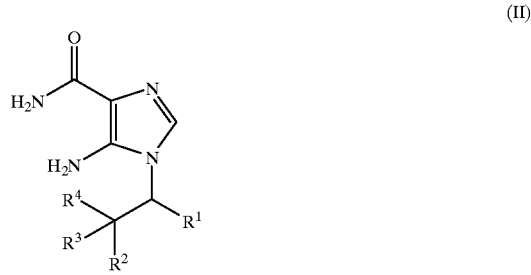

(II)

(where $R_1$, $R_2$, $R_3$, and $R_4$ have the meanings given above) with compounds of Formula III:

A—CO—Cl (III)

in which A has the meanings given above, in an inert solvent and in the presence of a base. This reaction produces a compound of Formula IV:

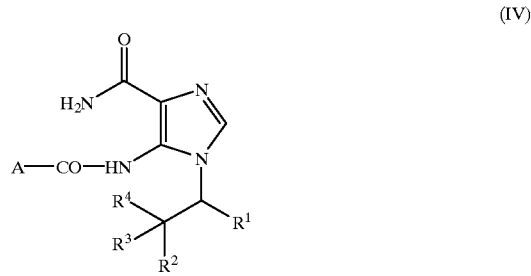

(IV)

in which A, $R_1$, $R_2$, $R_3$, and $R_4$ have the meanings given above. Such compounds are cyclized in a second step in an inert solvent and in the presence of a base, and the substituents $R_1$, $R_2$, $R^3$, and $R_4$ are introduced and derivatized by acylation, oxidation, and/or azide exchange.

The method of producing such compounds can be illustrated by way of example by the following schematic diagram:

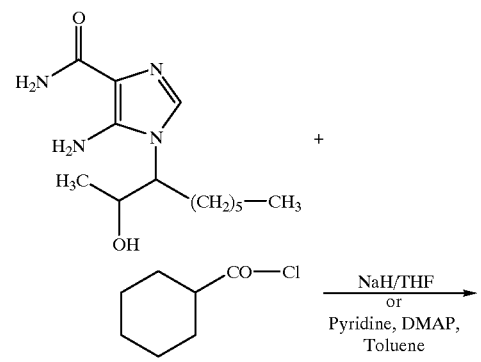

-continued

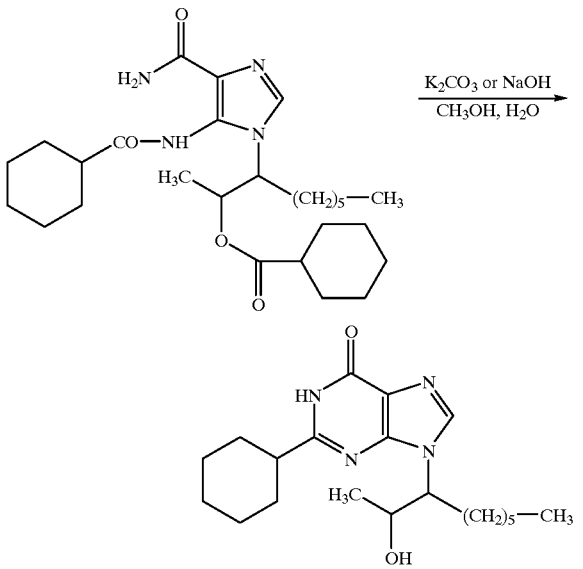

Inert organic solvents that do not change under the reaction conditions are suitable for the first step of the method. Preferred examples of them are ethers, for example diethyl ether, dioxane, tetrahydrofuran, ethylene glycol mono- or dimethyl ether, halogenated hydrocarbons such as di-, tri-, or tetrachloromethane, dichloroethylene, trichloroethylene, ethyl acetate, toluene, acetonitrile, hexamethylphosphoric triamide, pyridine, and acetone. Of course it is possible to use mixtures of solvents. Tetrahydrofuran, toluene, or pyridine are especially preferred.

Suitable bases include alkali metal hydrides or alkoxides (e.g., sodium hydride or potassium t-butoxide), cyclic amines (e.g., piperidine, pyridine, dimethylaminopyridine), or $C_1$–$C_4$-alkylamines (e.g., triethylamine). Sodium hydride, pyridine, and dimethylaminopyridine are preferred.

The base should be used in an amount of 1 mole to 4 moles, preferably from 1.2 moles to 3 moles, per mole of the compounds of Formula II.

The reaction temperature in general reportedly can be varied over a rather broad range. The operating temperature is generally in the range from –20° C. to 200° C., preferably from 0° C. to 25° C.

In a variant, the reaction is carried out in pyridine to which has been added a catalytic amount of DMAP. Toluene can also optionally be added.

Suitable solvents for the cyclization are the usual organic solvents. Preferred solvents are alcohols such as methanol, ethanol, propanol, isopropanol, or butanol, or ethers such as tetrahydrofuran or dioxane, or dimethylformamide or dimethyl sulfoxide. It is especially preferred to use alcohols such as methanol, ethanol, propanol, or isopropanol. It is likewise possible to use mixtures of the solvents mentioned.

Suitable bases for the cyclization are the usual inorganic bases. Preferred bases for this purpose are alkali metal hydroxides or alkaline earth hydroxides, for example sodium hydroxide, potassium hydroxide, or barium hydroxide, or alkali metal carbonates such as sodium or potassium carbonate, or sodium bicarbonate, or alkali metal alkoxides such as sodium methoxide, sodium ethoxide, potassium methoxide, potassium ethoxide, or potassium t-butoxide. Especially preferred are potassium carbonate and sodium hydroxide.

When carrying out the cyclization, the base is usually used in an amount of 2 to 6 moles, preferably from 3 to 5 moles, per mole of the compounds of Formula IV.

The cyclization is usually carried out in the temperature range of 0° C. to 160° C., preferably at the boiling point of the particular solvent.

The cyclization is usually carried out at atmospheric pressure. However, it is also possible to carry out the process at elevated or reduced pressure (for example, in the range from 0.5 to 5 bar).

The reaction with alkylsulfonyl chlorides occurs, starting from the corresponding free hydroxy compounds, in one of the solvents listed above and one of the bases, preferably with dichloromethane and triethylamine, in a temperature range from –20° C. to +20° C., preferably at 0° C. and atmospheric pressure.

The azide group is usually introduced by reacting the corresponding alkylsulfonyloxy-substituted compounds with sodium azide in one of the solvents listed above, preferably dimethylformamide, in a temperature range of 50° C. to +120° C., preferably at 100° C. and atmospheric pressure.

The ketones are prepared by known methods (Swern Oxidation) from the corresponding hydroxy compounds.

The enantiomerically pure compounds are available by the usual methods, for example by chromatography of the racemic compounds of the general formula (I) on chiral phases.

Many compounds of Formula III are reportedly known.

Compounds of Formula II can be prepared, for example, by reacting 2-amino-2-cyanoacetamide of Formula V:

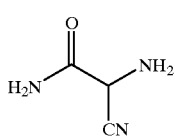

(V)

with a compound of Formula VI

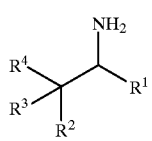

(VI)

in which $R_1$, $R_2$, $R_3$, and $R_4$ have the meanings given above in inert solvents in the presence of triethyl orthoformate. Solvents suitable for the individual steps of the process are the usual organic solvents that do not change under the reaction conditions. Preferred examples of them are ethers such as diethyl ether, dioxane, tetrahydrofuran, ethylene glycol dimethyl ether, or hydrocarbons such as benzene, toluene, xylene, hexane, cyclohexane, or petroleum fractions, or halogenated hydrocarbons such as dichloromethane, trichloromethane, tetrachloromethane, dichloroethylene, trichloroethylene, or chlorobenzene, or ethyl acetate, dimethylformamide, hexamethylphosphoramide, acetonitrile, acetone, or dimethoxyethane. It is likewise possible to use mixtures of the solvents mentioned. Acetonitrile is especially preferred.

The process of the invention is usually carried out in a temperature range of 0° C. to +180° C., preferably from +30° C. to +150° C.

These steps of the process pursuant to the invention are usually carried out at atmospheric pressure. However, it is also possible to operate at elevated pressure or reduced pressure (for example in range from 0.5 to 5 bar).

The compound of Formula V can be obtained as described in the literature [see. Logemann, G. Shaw, Chemistry and Industry, 1980 (13), 541–542].

The amines of Formula VI can then be prepared by known methods [see. L. R. Krepski et al., Synthesis, 1986, 301–303].

There are several methods to produce the 1-substituted 5-acylaminoimidazole-4-carboxamides of Formula IV, that are generally described below as Methods A and B.

Method A:

10 mmoles of the 1-substituted 5-aminoimidazole-4-carboxamide and 15 mmoles (or 30 mmoles if $R_2$ is hydroxy) of NaH (60% dispersion in mineral oil) in 50 ml of absolute THF are stirred for 3 hours at 20° C. (sparingly soluble imidazoles are refluxed for up to 3 hours). 10 mmoles of acid chloride (or 20 mmoles if a hydroxy group is present) in 2.5 ml of absolute THF is added dropwise at 20° C. and the mixture is stirred overnight at room temperature. The solvent is evaporated under vacuum in a rotary evaporator, and the residue is taken up in 50 ml of ethyl acetate and extracted with 50 ml of water. The organic phase is separated, dried over $NaSO_4$, and the solvent is evaporated under vacuum. The residue is purified by recrystallization or flash chromatography.

Method B:

10 mmoles of the 1-substituted-5-aminoimidazole-4-carboxamide is dissolved in 20 ml of dry pyridine. After adding 50 mg of 4-dimethylaminopyridine (DMAP), 11 mmoles of acid chloride (or 22 mmoles if $R_2$ is selected from the group consisting of a hydroxy group) is added dropwise at 20° C. (solid acid chlorides are dissolved in a little absolute toluene). The mixture is stirred for 1 h at 20° C.; in some cases 1–2 hours of heating at 50° C. is also necessary (TLC control). The batch is poured into 100 ml of ice water and extracted 3 times with 50-ml portions of ethyl acetate. The combined ethyl acetate phases are washed twice with 1 N HCl, once with saturated NaCl solution, dried over $NaSO_4$, and evaporated under vacuum. The residue is purified by flash chromatography or recrystallization.

The 1-substituted 5-acylaminoimidazole-4-carboxamides listed in Table I are prepared by these two methods:

TABLE I

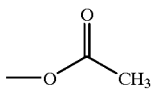

| 1) Example No. | A. | $R_4$ | $R_2$ | $R_1$ | 2) Method | 3) Yield (%) | $R_f$ |
|---|---|---|---|---|---|---|---|
| I | —$CH_3$ | $CH_3$ | 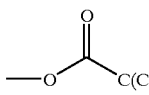 | n-Hexyl | A | 33 | 0.40 |
| II | —$C(CH_3)_3$ | $CH_3$ | 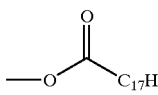 | n-Hexyl | A | 28 | 0.45 |
| III | -n-$C_{17}H_{35}$ | $CH_3$ | 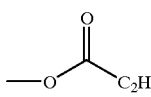 | n-Hexyl | B | 50 | 0.48 |
| IV | —$C_6H_5$ | $CH_3$ | 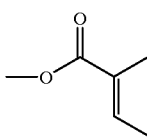 | n-Hexyl | A | 19 | 0.39 |
| V | -4-Cl—$C_6H_5$ | $CH_3$ |  | n-Hexyl | A | 15 | 0.40 |

TABLE I-continued

| 1) Example No. | A. | R$_4$ | R$_2$ | R$_1$ | 2) Method | 3) Yield (%) | R$_f$ |
|---|---|---|---|---|---|---|---|
| VI | cyclohexyl-CH< | CH$_3$ | -CH$_2$-O-C(=O)-cyclohexyl | n-Hexyl | B | 52 | 0.43 |
| VII | cyclohexyl-CH< | CH$_3$ | H | n-Hexyl | A | 16 | 0.38 |
| VIII | cyclohexyl-CH< | CH$_3$ | -CH$_2$-O-C(=O)-cyclohexyl | —CH$_2$CH$_2$-C$_6$H$_5$ | B | 45 | 0.41 |
| IX | cyclohexyl- | H | H | —CH$_2$CH$_2$-C$_6$H$_5$ | B | 41 | |
| X | phenyl- | H | H | —CH$_2$CH$_2$-C$_6$H$_5$ | B | 27.9 | |
| XI | 4-Cl-phenyl- | H | H | —CH$_2$CH$_2$-C$_6$H$_5$ | B | 17.3 | |
| XII | 4-Me-phenyl- | H | H | —CH$_2$CH$_2$-C$_6$H$_5$ | B | 37.9 | |
| XIII | isopropyl- | H | H | —CH$_2$CH$_2$-C$_6$H$_5$ | B | 29.2 | |
| XIV | cyclopropyl- | H | H | —CH$_2$CH$_2$-C$_6$H$_5$ | B | 38.7 | |
| XV | 4-NO$_2$-phenyl- | H | H | —CH$_2$CH$_2$-C$_6$H$_5$ | B | 15.7 | |

TABLE I-continued

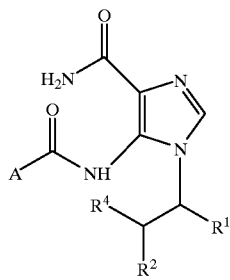

| 1) Example No. | A. | R₄ | R₂ | R₁ | 2) Method | 3) Yield (%) | R_f |
|---|---|---|---|---|---|---|---|
| XVI | 4-MeO-C₆H₄- | H | H | -CH₂CH₂CH₂-C₆H₅ | B | 18.3 | |
| XVII | 3-MeO-C₆H₄- | H | H | -CH₂CH₂CH₂-C₆H₅ | B | 44.7 | |
| XVIII | 2-MeO-C₆H₄- | H | H | -CH₂CH₂CH₂-C₆H₅ | B | | |
| XIX | cyclopentyl | H | H | -CH₂CH₂CH₂-C₆H₅ | B | 48 | |
| XX | 4-biphenyl | H | H | -CH₂CH₂CH₂-C₆H₅ | B | 34.8 | |
| XXI | 2-(CO₂Me)-cyclohexyl | H | H | -CH₂CH₂CH₂-C₆H₅ | B | 14.5 | |
| XXII | 4-(CO₂Me)-C₆H₄- | H | H | -CH₂CH₂CH₂-C₆H₅ | B | 11.4 | |
| XXIII | 3-(CO₂Me)-C₆H₄- | H | H | -CH₂CH₂CH₂-C₆H₅ | B | 28.7 | |
| XXIV | 3,4-(MeO)₂-C₆H₃- | H | H | -CH₂CH₂CH₂-C₆H₅ | B | 11.7 | |

TABLE I-continued

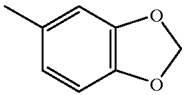

| 1) Example No. | A. | R₄ | R₂ | R₁ | 2) Method | 3) Yield (%) | $R_f$ |
|---|---|---|---|---|---|---|---|
| XXV | 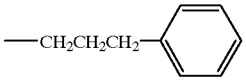 | H | H | —CH₂CH₂CH₂— 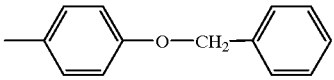 | B | | |
| XXVI | 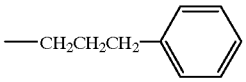 | H | H | —CH₂CH₂CH₂—  | B | | |
| XXVII | 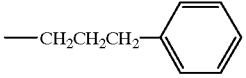 | H | H | —CH₂CH₂CH₂— 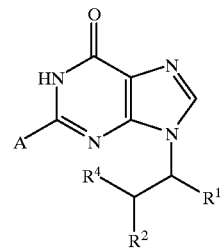 | B | 45 | 0.41 |

*Mobile phase: CH₂Cl₂/MeOH 10:1

There are several methods for making the 2,9-disubstituted purin-6-ones of Formula I that are set forth in Methods C and D below:

Method C:

1 mmole of 1-substituted 5-acylaminoimidazole-4-carboxamide and 5 mmoles of potassium carbonate are boiled at reflux overnight in 20 ml of ethanol and 10 ml of water. The solvent is evaporated under vacuum, and the residue is taken up in 20 ml of ethyl acetate and extracted with saturated NaCl solution. The organic phase is separated, dried over NaSO₄, and evaporated under vacuum. The residue is purified by recrystallization or flash chromatography.

Method D:

1 mmole of 1-substituted 5-acylaminoimidazole-4-carboxamide, 5 mmoles of potassium carbonate, and 1 ml of 30% H₂O₂ solution are boiled at reflux overnight in 10 ml of water and 10 ml of ethanol (TLC control). The further workup is the same as Method C. This method is reportedly analogous to that disclosed in EP Patent Application No. 526,004.

The 2,9-disubstituted purin-6-ones listed in Table II are prepared by these two methods:

TABLE II

| Example No. | A. | R₄ | R₂ | R₁ | Method | Yield (%) | $R_f$ |
|---|---|---|---|---|---|---|---|
| 1 | —CH₃ | CH₃ | OH | n-Hexyl | A | 68.6 | 0.38 (CH₂Cl₂/CH₃OH 10:1) |
| 2 | —C(CH₃)₃ | CH₃ | OH | n-Hexyl | A | 49.1 | 237 (ethyl acetate/ diethyl ether) |

TABLE II-continued

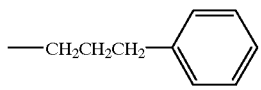

| Example No. | A. | R4 | R2 | R1 | Method | Yield (%) | Rf |
|---|---|---|---|---|---|---|---|
| 3 | -n-C$_{17}$H$_{35}$ | CH$_3$ | OH | n-Hexyl | B | 24.8 | 0.52 (CH$_2$Cl$_2$/CH$_3$OH 10:1) |
| 4 | —C$_6$H$_5$ | CH$_3$ | OH | n-Hexyl | A | 48.9 | 249 (ethyl acetate/diethyl ether) |
| 5 | -4-Cl—C$_6$H$_4$ | CH$_3$ | OH | n-Hexyl | A | 27.9 | 235 (C$_2$H$_5$OH/Ether) |
| 6 | —C$_6$H$_{11}$ | CH$_3$ | OH | n-Hexyl | B | 72.9 | 166 (ethyl acetate/diethyl ether) |
| 7 | —C$_6$H$_{11}$ | CH$_3$ | OH | n-Hexyl | A | 42.1 | 154 (ethyl acetate/diethyl ether) |
| 8 | —C$_6$H$_{11}$ | CH$_3$ | OH | —CH$_2$CH$_2$CH$_2$—C$_6$H$_5$ | B | 43.5 | 0.44 (CH$_2$Cl$_2$/CH$_3$OH 10:1) |
| 9 | 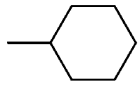 | H | H | —CH$_2$CH$_2$CH$_2$—C$_6$H$_5$ | A | 44.9 | 162° C. |
| 10 | 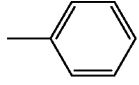 | H | H | —CH$_2$CH$_2$CH$_2$—C$_6$H$_5$ | A | 40.3 | 212° C. |
| 11 |  | H | H | —CH$_2$CH$_2$CH$_2$—C$_6$H$_5$ | A | 34.2 | 184° C. |
| 12 |  | H | H | —CH$_2$CH$_2$CH$_2$—C$_6$H$_5$ | A | 49.8 | 179° C. |
| 13 |  | H | H | —CH$_2$CH$_2$CH$_2$—C$_6$H$_5$ | A | 38.9 | 0.38 |
| 14 |  | H | H | —CH$_2$CH$_2$CH$_2$—C$_6$H$_5$ | A | 44.1 | 0.41 |
| 15 | 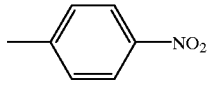 | H | H | —CH$_2$CH$_2$CH$_2$—C$_6$H$_5$ | A | 36 | 194° C. |
| 16 | 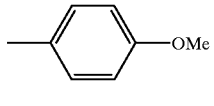 | H | H | —CH$_2$CH$_2$CH$_2$—C$_6$H$_5$ | A | 49.3 | 139° C. |

TABLE II-continued

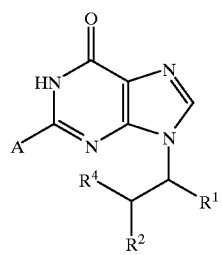

| Example No. | A. | R₄ | R₂ | R₁ | Method | Yield (%) | R_f |
|---|---|---|---|---|---|---|---|
| 17 | 3-MeO-C₆H₄- | H | H | -CH₂CH₂CH₂-C₆H₅ | A | 41.7 | 125° C. |
| 18 | 2-MeO-C₆H₄- | H | H | -CH₂CH₂CH₂-C₆H₅ | A | | |
| 19 | cyclopentyl- | H | H | -CH₂CH₂CH₂-C₆H₅ | A | 48.9 | 149° C. |
| 20 | 4-Ph-C₆H₄- | H | H | -CH₂CH₂CH₂-C₆H₅ | A | 32.5 | 164° C. |
| 21 | 2-(CO₂H)-cyclohexyl- | H | H | -CH₂CH₂CH₂-C₆H₅ | A | 35.1 | 128° C. |
| 22 | 4-(CO₂H)-C₆H₄- | H | H | -CH₂CH₂CH₂-C₆H₅ | A | 29.2 | 235° C. (Zers.) |
| 23 | 3-(CO₂H)-C₆H₄- | H | H | -CH₂CH₂CH₂-C₆H₅ | A | 44.6 | 243° C. (Zers.) |
| 24 | 3,4-(MeO)₂-C₆H₃- | H | H | -CH₂CH₂CH₂-C₆H₅ | A | 37.1 | 195° C. |
| 25 | 3,4-methylenedioxy-C₆H₃- | H | H | -CH₂CH₂CH₂-C₆H₅ | A | 42.6 | 182° C. |

TABLE II-continued

| Example No. | A. | R₄ | R₂ | R₁ | Method | Yield (%) | R_f |
|---|---|---|---|---|---|---|---|
| 26 | [4-(benzyloxy)phenyl] | H | H | —CH₂CH₂CH₂—phenyl | A | 41.1 | 245° C. |
| 27 | [4-bromophenyl] | H | H | —CH₂CH₂CH₂—phenyl | A | 32.7 | 190° C. |
| 28 | [4'-methoxybiphenyl] | H | H | —CH₂CH₂CH₂—phenyl | A | 35 | 152° C. |

The following Examples further illustrate compounds useful in the practice of this invention.

EXAMPLE 29

9-(2-Methanesulfonyloxy-3-Nonyl)-2-Cyclohexylpurin-6-One

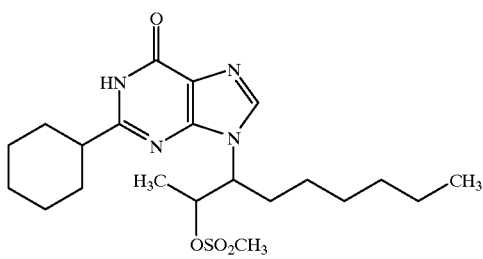

0.36 g (1 mmole) of 9-(2-hydroxy-3-nonyl)-2-cyclohexylpurin-6-one (Example 6) and 0.3 ml of triethylamine are stirred in 5 ml of absolute $CH_2Cl_2$ at 0° C. 0.1 ml of methanesulfonyl chloride dissolved in 2.5 ml of absolute $CH_2Cl_2$ is then added dropwise. After 30 minutes at 0° C., the mixture is extracted with 10 ml of saturated $NaHCO_3$ solution, 10 ml of 2 N HCl solution, and with 10 ml of saturated $NaHCO_3$ solution. The organic phase is dried over $Na_2SO_4$, the solvent is evaporated under vacuum, and the residue is purified by flash chromatography with ethyl acetate/$CH_2Cl/CH_3OH$ 10:1 as eluant.

EXAMPLE 30

9-(2-Methanesulfonyl-6-Phenyl-3-Hexyl)-2-Cyclohexylpurin-6-One

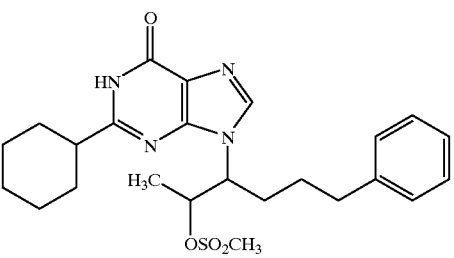

The title compound is prepared analogously to the method of Example 29 starting with 9-(2-hydroxy-6-phenyl-3-hexyl)-2-cyclohexylpurin-6-one (Example 8).

EXAMPLE 31

9-(2-Azido-3-Nonyl)-2-Cyclohexylpurin-6-One

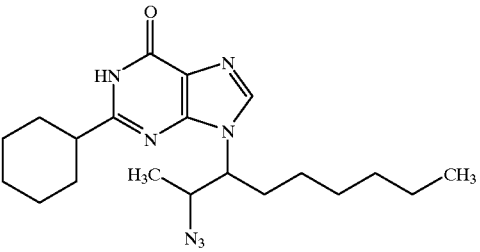

0.381 g (0.87 mmole) of 9-(2-methanesulfonyloxy-3-nonyl)-2-cyclohexylpurin-6-one (Example 29) and 0.113 g (1.74 mmoles) of sodium azide are stirred overnight at 100° C. in 5 ml of absolute DMF. The mixture is cooled to 20° C., 30 ml of ethyl acetate is added, and the mixture is washed twice with 50-ml portions of water and once with 50 ml of saturated NaCl solution. After

EXAMPLE 32

9-(2-Azido-6-Phenyl-3-Hexyl)-2-Cyclohexylpurin-6-One

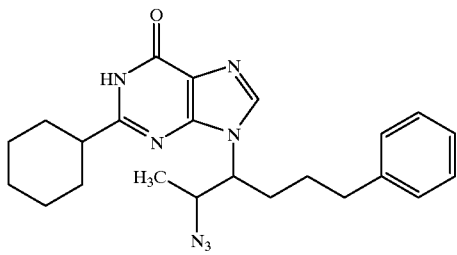

The title compound is prepared analogously to the method of Example 31 starting with 9-(2-methanesulfonyloxy-6-phenyl-3-hexyl)-2-cyclohexylpurin-6-one (Example 30).

EXAMPLE 33

9-(2-Oxo-3-Nonyl)-2-Cyclohexylpurin-6-One

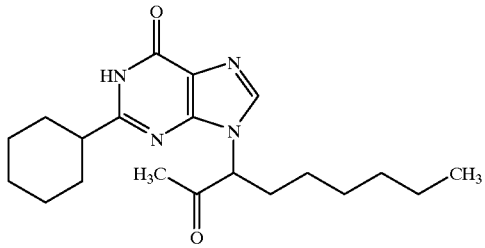

0.2 ml of absolute DMSO in 3 ml of absolute CH$_2$Cl$_2$ is added dropwise at −60° C. to 0.15 ml of oxalyl chloride in 5 ml of absolute CH$_2$Cl$_2$, and stirring is continued for 20 minutes longer. 540 mg (1.5 mmoles) of 9-(2-hydroxy-3-nonyl)-2-cyclohexylpurin-6-one (Example 6) in 3 ml of CH$_2$Cl$_2$ is then added dropwise and slowly and stifling is continued for 1 hour at 60° C. 1 ml of triethylamine in 3 ml of CH$_2$Cl$_2$ is added dropwise to this solution. The mixture is allowed to come to room temperature, 7 ml of water is added, and the organic phase is separated. The organic phase is washed with 10 ml of 2 N HCl and 10 ml of saturated NaCl solution, dried over Na$_2$SO$_4$, and evaporated under vacuum. The residue is purified by flash chromatography (eluant: CH$_2$Cl$_2$/CH$_3$OH 40:1)

EXAMPLE 34

9-(2-Oxo-6-Phenyl-3-Hexyl)-2-Cyclohexylpurin-6-One

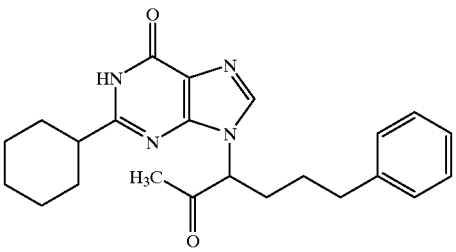

The title compound is prepared analogously to the method of Example 33 starting with 9-(2-hydroxy-6-phenyl-3-hexyl)-2-cyclohexylpurin-6-one (Example 8).

It will be understood that various changes and modifications can be made in the details of procedure, formulation and use without departing from the spirit of the invention, especially as defined in the following claims.

We claim:

1. A method for inhibiting the growth of neoplastic cells sensitive to a compound below comprising exposing the cells to a growth inhibiting effective amount of a compound of Formula

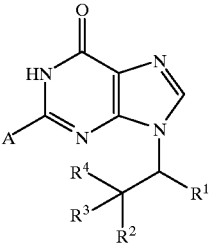

wherein $R_1$ is selected from the group consisting of straight-chain or branched alkyl with 2 to 10 carbon atoms, which is optionally substituted by phenyl, which in turn may be substituted by halogen, nitro, cyano, or by straight-chain or branched alkyl with up to 6 carbon atoms;

$R_2$ is selected from the group consisting of hydrogen, hydroxy, azido, or a straight-chain or branched alkyl with up to 6 carbon atoms, or a group with the formula —O—SO$_2$R$_5$;

$R_5$ is selected from the group consisting of a straight-chain or branched alkyl with up to 4 carbon atoms or phenyl;

$R_3$ is selected from the group consisting of hydrogen or $R_2$ and $R_3$ together form a group of the formula =O;

$R_4$ is selected from the group consisting of hydrogen or a straight-chain or branched alkyl with up to 4 carbon atoms; and A is selected from the group consisting of a moiety of the formula:

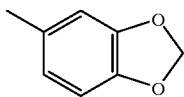

or a straight-chain or branched alkyl with up to 20 carbon atoms, or a cycloalkyl with 3 to 7 carbon atoms, phenyl wherein said moiety, alkyl, cycloalkyl or phenyl groups are optionally substituted with one or two groups independently selected from the group consisting of halogen, carboxyl, trifluoromethyl, nitro, hydroxy, cyano, or straight-chain or branched alkyl, alkoxycarbonyl, or alkoxy, each with up to 5 carbon atoms, which in turn may be substituted by phenyl, said ring structures optionally substituted by phenyl, which in turn may be substituted by straight-chain or branched alkoxy with up to 5 carbon atoms; and their tautomers and salts.

2. The method according to claim 1 wherein $R_1$ is selected from the group consisting of straight-chain or branched alkyl with 2 to 8 carbon atoms, which is optionally substituted by phenyl, which in turn may be substituted by fluorine; chlorine, bromine, nitro, cyano, or by straight-chain or branched alkyl with up to 4 carbon atoms, $R_2$ is selected from the group consisting of hydrogen, hydroxy, azido, or for straight-chain or branched alkyl with up to 4 carbon atoms, or a group with the formula —O—$SO_2R_5$;

$R_5$ is selected from the group consisting of straight-chain or branched alkyl with up to 3 carbon atoms, or phenyl;

$R_4$ is selected from the group consisting of hydrogen or for straight-chain or branched alkyl with up to 3 carbon atoms; and A is selected from the group consisting of a moiety of the formula

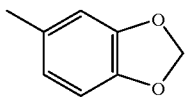

or straight-chain or branched alkyl with up to 19 carbon atoms, or for cyclopropyl, cyclopentyl, cyclohexyl, cycloheptyl, or for phenyl, which optionally are substituted with one or two groups independently selected from the group consisting of fluorine, chlorine, bromine, carboxyl, nitro, hydroxy, or by straight-chain or branched alkyl, alkoxycarbonyl, or alkoxy, each with up to 4 carbon atoms, which in turn may be substituted by phenyl, said ring structures optionally are optionally substituted by phenyl, which in turn may be substituted by straight-chain or branched alkoxy with up to 4 carbon atoms and their tautomers and salts.

3. The method according to claim 1 wherein $R_1$ is selected from the group consisting of straight-chain or branched alkyl with 2 to 7 carbon atoms, which is optionally substituted by phenyl, which in turn may be substituted by fluorine, chlorine, bromine, nitro, cyano, or by straight-chain or branched alkyl with up to 3 carbon atoms;

$R_2$ is selected from the group consisting of hydrogen, hydroxy, azido, or a straight-chain or branched alkyl with up to 3 carbon atoms, or for a group with the formula —O—$SO_2R_5$;

$R_5$ is selected from the group consisting of straight-chain or branched alkyl with up to 3 carbon atoms or phenyl, $R_3$ is selected from the group consisting of hydrogen or $R_2$ and $R_3$ jointly form the group of the formula =O, $R_4$ is selected from the group consisting of hydrogen or a straight-chain or branched alkyl with up to 3 carbon atoms; and A is selected from the group consisting of a group of the formula

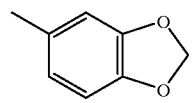

or for straight-chain or branched alkyl with up to 18 carbon atoms, or cyclopropyl, cyclopentyl, cyclohexyl, cycloheptyl, or for phenyl, which optionally are substituted up to twice with the same or different substituents consisting of fluorine, chlorine, bromine, carboxyl, nitro, hydroxy, or by straight-chain or branched alkyl, alkoxycarbonyl, or alkoxy, each with up to 3 carbon atoms, which in turn may be substituted by phenyl, and/or the rings are optionally substituted by phenyl, which in turn may be substituted by straight-chain or branched alkoxy with up to 3 carbon atoms; and their tautomers and salts.

4. A method of treating a mammal having precancerous lesions sensitive to a compound below comprising administering to said mammal a pharmacologically effective amount of a compound of Formula I:

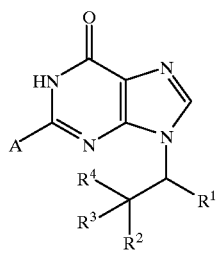

wherein $R_1$ is selected from the group consisting of straight-chain or branched alkyl with 2 to 10 carbon atoms, which is optionally substituted by phenyl, which in turn may be substituted by halogen, nitro, cyano, or by straight-chain or branched alkyl with up to 6 carbon atoms;

$R_2$ is selected from the group consisting of hydrogen, hydroxy, azido, or a straight-chain or branched alkyl with up to 6 carbon atoms, or a group with the formula —O—$SO_2R_5$;

$R_5$ is selected from the group consisting of a straight-chain or branched alkyl with up to 4 carbon atoms or phenyl;

$R_3$ is selected from the group consisting of hydrogen or $R_2$ and $R_3$ together form a group of the formula =O;

$R_4$ is selected from the group consisting of hydrogen or a straight-chain or branched alkyl with up to 4 carbon atoms; and A is selected from the group consisting of a moiety of the formula:

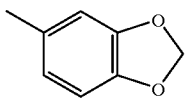

or a straight-chain or branched alkyl with up to 20 carbon atoms, or a cycloalkyl with 3 to 7 carbon atoms, phenyl wherein said moiety, alkyl, cycloalkyl or phenyl groups are optionally substituted with one or two groups independently selected from the group consisting of halogen, carboxyl, trifluoromethyl, nitro, hydroxy, cyano, or straight-chain or branched alkyl, alkoxycarbonyl, or alkoxy, each with up to 5 carbon atoms, which in turn may be substituted by phenyl, said ring structures optionally substituted by phenyl, which in turn may be substituted by straight-chain or branched alkoxy with up to 5 carbon atoms; and their tautomers and salts.

5. The method according to claim 4 wherein $R_1$ is selected from the group consisting of straight-chain or branched alkyl with 2 to 8 carbon atoms, which is optionally substituted by phenyl, which in turn may be substituted by fluorine; chlorine, bromine, nitro, cyano, or by straight-chain or branched alkyl with up to 4 carbon atoms, $R_2$ is selected from the group consisting of hydrogen, hydroxy, azido, or for straight-chain or branched alkyl with up to 4 carbon atoms, or a group with the formula —O—$SO_2R_5$;

$R_5$ is selected from the group consisting of straight-chain or branched alkyl with up to 3 carbon atoms, or phenyl;

$R_4$ is selected from the group consisting of hydrogen or for straight-chain or branched alkyl with up to 3 carbon atoms; and A is selected from the group consisting of a moiety of the formula

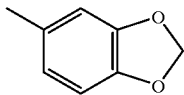

or straight-chain or branched alkyl with up to 19 carbon atoms, or for cyclopropyl, cyclopentyl, cyclohexyl, cycloheptyl, or for phenyl, which optionally are substituted with one or two groups independently selected from the group consisting of fluorine, chlorine, bromine, carboxyl, nitro, hydroxy, or by straight-chain or branched alkyl, alkoxycarbonyl, or alkoxy, each with up to 4 carbon atoms, which in turn may be substituted by phenyl, said ring structures optionally are optionally substituted by phenyl, which in turn may be substituted by straight-chain or branched alkoxy with up to 4 carbon atoms and their tautomers and salts.

6. The method according to claim 4 wherein R, is selected from the group consisting of straight-chain or branched alkyl with 2 to 7 carbon atoms, which is optionally substituted by phenyl, which in turn may be substituted by fluorine, chlorine, bromine, nitro, cyano, or by straight-chain or branched alkyl with up to 3 carbon atoms;

$R_2$ is selected from the group consisting of hydrogen, hydroxy, azido, or a straight-chain or branched alkyl with up to 3 carbon atoms, or for a group with the formula —O—$SO_2R_5$;

$R_5$ is selected from the group consisting of straight-chain or branched alkyl with up to 3 carbon atoms or phenyl, $R_3$ is selected from the group consisting of hydrogen or $R_2$ and $R_3$ jointly form the group of the formula =O, $R_4$ is selected from the group consisting of hydrogen or a straight-chain or branched alkyl with up to 3 carbon atoms; and A is selected from the group consisting of a group of the formula or for straight-chain or branched alkyl with up to 18 carbon atoms, or cyclopropyl, cyclopentyl, cyclohexyl, cycloheptyl, or for phenyl, which optionally are substituted up to twice with the same or different substituents consisting of fluorine, chlorine, bromine, carboxyl, nitro, hydroxy, or by straight-chain or branched alkyl, alkoxycarbonyl, or alkoxy, each with up to 3 carbon atoms, which in turn may be substituted by phenyl, and/or the rings are optionally substituted by phenyl, which in turn may be substituted by straight-chain or branched alkoxy with up to 3 carbon atoms; and their tautomers and salts.

* * * * *